US009833168B2

(12) United States Patent
Schweitzer et al.

(10) Patent No.: US 9,833,168 B2
(45) Date of Patent: Dec. 5, 2017

(54) NOISE TOLERANT LOCALIZATION SYSTEMS AND METHODS

(75) Inventors: Jeffrey A. Schweitzer, St. Paul, MN (US); D. Curtis Deno, Andover, MN (US); Timothy G. Curran, Ramsey, MN (US); Larry J. Hull, Scandia, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 470 days.

(21) Appl. No.: 14/123,698

(22) PCT Filed: Apr. 18, 2012

(86) PCT No.: PCT/US2012/034032
§ 371 (c)(1),
(2), (4) Date: Dec. 3, 2013

(87) PCT Pub. No.: WO2012/170119
PCT Pub. Date: Dec. 13, 2012

(65) Prior Publication Data
US 2014/0128722 A1    May 8, 2014

Related U.S. Application Data

(60) Provisional application No. 61/493,855, filed on Jun. 6, 2011.

(51) Int. Cl.
*A61B 5/06*     (2006.01)
*A61B 5/00*     (2006.01)
(Continued)

(52) U.S. Cl.
CPC ............ *A61B 5/062* (2013.01); *A61B 5/0402* (2013.01); *A61B 5/042* (2013.01); *A61B 5/055* (2013.01);
(Continued)

(58) Field of Classification Search
CPC .......... A61B 5/055; A61B 5/06; A61B 5/061; A61B 5/062; A61B 5/063; A61B 34/20;
(Continued)

(56) References Cited

U.S. PATENT DOCUMENTS 5,529,068 A    6/1996  Hoenninger, III et al.
6,073,039 A    6/2000  Berson
(Continued)

FOREIGN PATENT DOCUMENTS

WO    WO 03/100450    12/2003
WO    WO 2005/116676  12/2005
WO    WO 2011/090594   7/2011

OTHER PUBLICATIONS

International Search Report and Written Opinion issued in International (PCT) Patent Application No. PCT/US2012/034032 (Aug. 10, 2012).

*Primary Examiner* — Peter Luong
(74) *Attorney, Agent, or Firm* — Dykema Gossett PLLC

(57) ABSTRACT

A system and method for tracking catheter electrode locations with the body of a patient during an MRI scan sequence includes mitigation logic configured to identify one or more impedance measurements that were taken during potentially noise-inducing conditions (i.e., magnet gradients, RF pulses), and were thus subject to corruption by noise. The mitigation logic is configured to replace the potentially corrupt impedance measurements with previously-obtained impedance measurements taken from an immediately preceding acquisition cycle (e.g., from a previous time-slice).

20 Claims, 10 Drawing Sheets

(51) Int. Cl.

| | | |
|---|---|---|
| *A61B 5/0402* | (2006.01) | |
| *A61B 5/042* | (2006.01) | |
| *A61B 5/055* | (2006.01) | |
| *G01R 33/567* | (2006.01) | |
| *A61B 34/20* | (2016.01) | |
| *A61B 18/14* | (2006.01) | |
| *A61B 90/00* | (2016.01) | |

(52) U.S. Cl.
CPC ............ *A61B 5/063* (2013.01); *A61B 5/7203* (2013.01); *A61B 5/7217* (2013.01); *A61B 5/7264* (2013.01); *A61B 34/20* (2016.02); *G01R 33/5673* (2013.01); *A61B 18/1492* (2013.01); *A61B 2090/374* (2016.02)

(58) Field of Classification Search
CPC .......... A61B 2090/374; A61B 18/1492; G01R 33/5673
See application file for complete search history.

(56) References Cited

U.S. PATENT DOCUMENTS

| | | |
|---|---|---|
| 6,255,820 B1 | 7/2001 | Steckner |
| 6,900,638 B1 | 5/2005 | Yair et al. |
| 7,012,428 B1 | 3/2006 | Ward et al. |
| 7,375,522 B2 | 5/2008 | Reeder |
| 7,706,855 B1 | 4/2010 | Priatna et al. |
| 7,945,305 B2 | 5/2011 | Aggarwal et al. |
| 2004/0097802 A1 | 5/2004 | Cohen |
| 2005/0261571 A1 | 11/2005 | Willis |
| 2007/0060833 A1 | 3/2007 | Hauck |
| 2008/0200973 A1 | 8/2008 | Mallozzi et al. |
| 2008/0300504 A1 | 12/2008 | Lefkov |
| 2009/0012387 A1 | 1/2009 | Hanson et al. |
| 2009/0254140 A1 | 10/2009 | Rosenberg |
| 2010/0090693 A1 | 4/2010 | Wald et al. |
| 2010/0264922 A1 | 10/2010 | Xu |
| 2010/0280353 A1 | 11/2010 | Roth et al. |
| 2011/0156706 A1 | 6/2011 | Stubbs et al. |
| 2011/0166436 A1 | 7/2011 | Edelman |

NOISE TOLERANT LOCALIZATION SYSTEMS AND METHODS

CROSS-REFERENCE TO RELATED APPLICATIONS

This application claims the benefit of U.S. provisional application No. 61/493,855, filed 6 Jun. 2011, which is hereby incorporated by reference as though fully set forth herein.

FIELD OF THE INVENTION

The field of the invention relates to systems and apparatus for generating three dimensional (3D) organ geometries and tracking medical devices in vivo and methods of real-time tracking of same. More particularly, the invention relates to such geometry generation (including electro-anatomic mapping (EAM)), during a medical imaging process.

BACKGROUND OF THE INVENTION

The electrocardiogram (ECG) is a widely used clinical tool for cardiac physiological monitoring and for the real-time diagnosis of heart conditions. Surface ECG monitoring, in which the ECG electrodes are attached to a patient's skin, is one type of ECG monitoring that is often used with medical imaging processes. Frequently, patients with cardiac conditions will undergo, for example, a magnetic resonance imaging (MRI) scan in which ECG information is monitored during the scan sequence and used to assist in MRI image acquisition. The ECG information that is obtained may be used, for example, for properly synchronizing cardiac MRI scans, which is a process typically referred to as "gating." Because cardiovascular anatomy is continuously moving throughout the MRI scan, synchronization or "gating" of MRI data acquisition with the cardiac cycle allows for improved imaging of the cardiovascular anatomy at the various phases of the cardiac cycle. Surface ECG monitoring is also frequently used for physiological monitoring of patients who are being scanned for multiple indications (brain, knee, abdomen, etc.) or who are undergoing therapeutic interventions inside the MRI (even interventions not within the cardiovascular system). This is especially true for patients who are anesthetized during the scan or who have a history of heart disease or of stroke.

Surface ECG monitoring inside an MRI scanner presents several challenges that can affect the quality, and thus the usability, of the ECG signals and MRI data acquired. First, the ECG electrodes can experience unwanted voltages that are induced during the ramping up and down of the magnetic field gradients used in the MRI scan. Due to the changing magnetic field caused by the gradient rampings, current is induced in the ECG electrodes, with amplitudes up to a few volts. These induced voltages can be many times larger than the voltage levels of the true ECG signals and, therefore, can saturate the ECG acquisition equipment, making the true ECG signals more difficult to accurately filter out and detect. And, the higher voltages can potentially damage the ECG acquisition equipment, which is configured to ordinarily detect only measurements in the range of a few milli-volts. Additionally, the induced voltages can have a frequency content of anywhere between about 100-10,000 Hz, which can render it very difficult to remove the unwanted induced signals with simple frequency filters. Similarly, the ECG electrodes and leads may conduct radio frequency (RF) fields, such as 64 MHz for 1.5T or 127 MHz for 3T, which are induced into the ECG electrodes and leads by the MRI scan sequence's RF pulses. These RF-induced signals cause further noise and, thus, also deteriorate the quality of the signals acquired by the ECG electrodes. Not only do these phenomena negatively affect the acquisition of ECG information, they can interfere with acquiring the desired imaging data.

Attempts have been made to address the issues confronting use of surface ECG monitoring inside an MRI scanner, but have met with only limited success. Most attempted solutions have simply taken the approach of using a smaller number of ECG electrodes (typically around 3 to 5 electrodes) that are closely distanced from each other in order to, in theory, reduce the induced RF and gradient voltages. However, 12-lead ECG surface monitoring arrangements, in which electrodes are placed at designated positions on the torso, is the preferred and most widely used system for monitoring heart condition. Reducing the number of electrodes to only 3 to 5, and arranging the electrodes much more closely than the standard 12-lead arrangement, causes the quality and usefulness of the ECG signals to be severely deteriorated. As a result, such approaches are useful only to perform MRI scan synchronization and do not provide physiological monitoring-quality ECG traces.

Other attempted solutions have involved the use of software filtering or digital signal processing of the acquired ECG signals to remove or suppress the RF and gradient induced components in the ECG leads, but these have met with limited success and also do not provide physiological monitoring-quality traces. Noise caused by gradient ramping and RF transmission during an MRI scan sequence is intrinsically a difficult problem to address with software and digital signal processing, because the gradient noise component in ECG leads is on the order of a thousand times stronger than the true ECG signal component. In addition, because the gradient fields applied by MR systems constantly change to a significant degree in terms of magnitude, direction, frequency, and duration (due to different requirements of each imaging sequence), it is difficult or impossible for signal-processing algorithms to adapt to the large variety of potential gradient noise.

Electro-Anatomic-Mapping (EAM) is a relatively newer clinical tool than traditional surface ECG monitoring, in which ECG data is collected at various positions inside the body, including on the walls of the cardiac chambers. One of the distinguishing differences from surface ECG monitoring is that positional information is also acquired on the same conductive lines as the ones that transfer the ECG signals from the electrodes to the receiver. This positional information is acquired, for example, by inducing electrical currents from surface electrodes and sampling them using catheters that have multiple electrodes on their shaft and that are moved inside the body. The positional tracking signals are generally electromagnetic signals at higher frequencies (5-10 kHz) then those found in conventional ECG (0-300 Hz), so they are easily separated by the EAM receiver. The common practice is to display the position of the catheter electrodes and the ECG voltage at those points, which defines the EAM map. Available EAM systems include the NavX™ systems offered by St. Jude Medical, Inc. and the Carto systems offered by Biosense Webster, Inc.

However, like surface ECG monitoring, EAM mapping inside an MRI scanner also presents several issues that can affect signal quality. First, the ECG component of EAM signals encounters the same RF and gradient induced noise problems as discussed above. Second, the positional localization component of the EAM signals suffer from the induced voltages caused by the gradient ramps as well, since the noise created by the gradient ramps is within the same reception band (5-10 kHz) of the localization voltages. For example, one type of NavX™ system operates using a 5.8 kHz signal, while others operate with 8.1 kHz signals.

These issues confronting the use of EAM inside an MRI scanner have either not been addressed at all, or have only been addressed by an unsatisfactory solution. In fact, the only techniques currently in accepted use that offer positional information in MRI scanners are either based on passive tracking (i.e., using the MRI images themselves for following interventional devices) or use MRI techniques for active tracking (e.g., MR-tracking or MRI-gradient tracking). These solutions do not work outside the MRI scanner, so they cannot be used to monitor a patient during transfer in and out of the scanner, during portions of the procedure which are conducted outside the MRI bore, or during periods in which the patient is inside the scanner, but no images are being acquired.

Moreover, the issues confronting acquisition of ECG and EAM information during an MRI scan can also negatively impact the use of other physiological monitoring tools, such as pulse oximeters, blood pressure cuffs, and respiratory monitors. Each of these clinical tools may include the use of electrodes and leads that can also be susceptible to the same unwanted currents and voltages induced by gradient ramping and RF transmission occurring during an MRI scan.

It would therefore be desirable to provide a system and method for reducing or avoiding the negative effects of RF and gradient induced voltages on ECG and EAM signals (and other physiological monitoring signals), to allow for acquisition of physiological monitoring-quality ECG and/or EAM signals from inside an MRI scanner during a scan. Similarly, it would be further desirable if the system and method allowed for acquisition of such signals both inside and outside the scanner and during periods in which images are being acquired and not being acquired.

SUMMARY OF THE INVENTION

A noise-tolerant apparatus for determining a position of an electrode of an invasive medical device includes an electronic control unit (ECU) and a computer-readable memory coupled to said ECU. The apparatus further includes position determining logic configured to determine the device electrode position based on a plurality of impedance measurements taken with respect to the electrode. The apparatus further includes mitigation logic configured to identify one or more of the impedance measurements taken during an external noise inducing condition and which are subject to corruption. The mitigation logic is further configured to replace the one or more identified impedance measurements in accordance with a predetermined mitigation strategy.

In another embodiment, the mitigation logic is configured to substitute one or more previously-obtained impedance measurements for the identified one or more impedance measurements in accordance with a predetermined mitigation strategy.

In a further embodiment, an article of manufacture is provided. The article of manufacture includes a computer storage medium having a computer program encoded thereon for determining a device electrode position of an invasive medical device based on a plurality of impedance measurements taken with respect to the electrode. The computer program is further configured for identifying one or more of the impedance measurements taken during an external noise inducing condition and which are subject to corruption. The program is also configured for replacing the one or more identified impedance measurements in accordance with a predetermined mitigation strategy.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
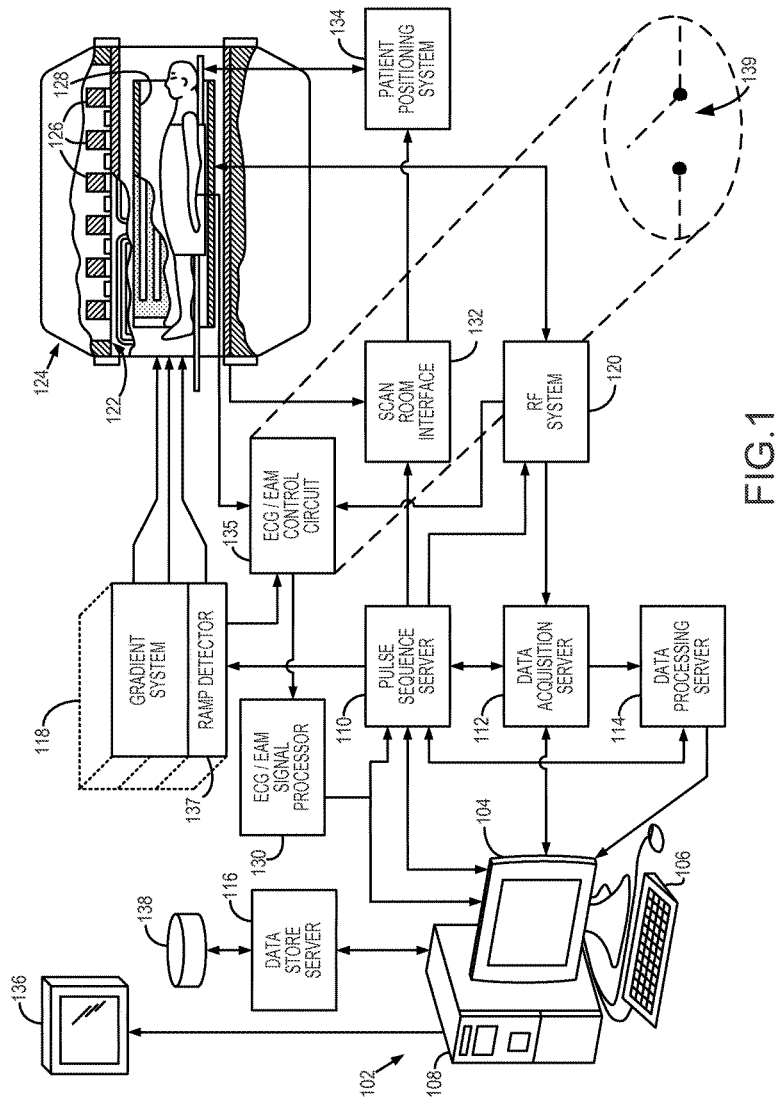
FIG. 1 is a block diagram of an exemplary magnetic resonance imaging ("MRI") system in which ECG/EAM signal gating control and processing circuits are integrated with the MRI system in accordance with the present invention.

Referring particularly to FIG. 1, the present invention is employed in a magnetic resonance imaging ("MRI") system. The MRI system includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radio frequency ("RF") system 120. Gradient waveforms necessary to perform the prescribed scan are produced and applied to the gradient system 118, which excites gradient coils in a gradient coil assembly 122 to produce the magnetic field gradients $G_x$, $G_y$, and $G_z$ used for position encoding MR signals. The gradient coil assembly 122 forms a part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the $I$ and $Q$ components:

$$M = \sqrt{I^2 + Q^2} \qquad \text{Eqn. (1);}$$

and the phase of the received MR signal may also be determined:

$$\phi = \tan^{-1}\left(\frac{Q}{I}\right). \qquad \text{Eqn. (2)}$$

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

In some scans, the pulse sequence server 110 may optionally receive physiological patient monitoring signals from a number of different sensors connected to the patient, such as ECG or EAM signals from electrodes and associated interventional catheters, pulse oximeter signals, signals from a blood pressure cuff, or respiratory signals from a bellows or other respiratory monitoring device. In the embodiment depicted in FIG. 1, ECG or EAM signals are acquired from a patient inside the MRI scanner during a scan and are transmitted via an ECG/EAM signal gating control circuit 135 to an ECG/EAM signal receiver or processor 130. Preferably, the ECG or EAM signals are conducted using low-noise cables, to reduce interference inside the scan room. The processor 130 conditions, filters, and/or processes the raw signals and ultimately transmits ECG and/or EAM information to the workstation 102 and/or the pulse sequence server 110. Alternatively, the functionality of the processor 130 may be integrated with the workstation 102 or other component of the MRI system, or may include a commercial ECG or EAM receiving and processing system such as, for example, a Cardiolab Electrophysiology Recording System offered by GE Healthcare or the NavX™ system offered by St. Jude Medical, Inc.

The signal gating control circuit 135 may be responsive to a variety of control signals to coordinate ECG and EAM acquisition with operation of gradient system 118 and RF system 120. As discussed above, the ramping up and down of the gradient fields as well as certain RF transmissions can seriously degrade the quality of output from ECG and EAM electrodes, as well as other physiological monitoring devices. Thus, during periods of an imaging sequence that cause induced voltages and noise in the output of the ECG and EAM electrodes (such as gradient ramping and RF transmission), output from the ECG and EAM electrodes can be disconnected or discarded by control circuit 135 so as to limit the effect of the unwanted noise on patient monitoring and MRI image acquisition. For example, in the embodiment shown, control circuit 135 is responsive to gating signals from the RF system 120 and a gradient ramp detection circuit 137 integrated with the gradient system 118. These gating signals may be, for example, TTL (transistor-transistor logic) signals used to cause the control circuit 135 to alternately disconnect the output of the electrodes from the processor 130 or connect the output of the electrodes to the processor 130.

Accordingly, signal gating control circuit 135 may comprise a switch that alternately opens to disconnect or impede output of the ECG or EAM electrodes and closes to communicate output of the electrodes to processor 130, in according with control signals from the gradient system 118 and RF system 120. Such a switch may include solid-state, fast-response electronics to ensure a rapid disconnection and reconnection of the real-time ECG or EAM acquisition during and after the gradient ramps. Desirable switching delay times are less than 200 nsec, though it is understood that other switching times may be acceptable. In one embodiment, the switch could comprise a single pole double throw electronic switch. Thus, as depicted in FIG. 1, control circuit 135 may include a switch 139 connected between the patient electrodes and the processor 130.

Alternatively, as will also be discussed below with respect to FIG. 2, control circuit 135 may include a system for discarding or ignoring signals output by the electrodes (or other physiological monitoring tool) during periods of induced noise (such as during gradient ramping or RF transmission). In such an implementation, software algorithms may be used that analyze control signals from the gradient system 118 and RF system 120 as timing signals to blank, discard, or ignore ECG or EAM acquisition during periods of induced noise. Such software may be executed on processor 130, or the functionality of control circuit 135 and processor 130 may both be integrated with workstation 104 or other computational component of the MRI system. Alternatively, control circuit 135 may comprise a software algorithm that is implemented by a digital signal processing circuit for removing output from the electrodes during periods of induced noise from the signal transmission stream to the processor 130. In other words, control circuit 135 may include a switch, circuit, chip, or software algorithm for preventing use of signals output by patient physiological condition sensors during periods of noise induced by operation of the gradient system 118 and/or RF system 120 during an MRI scan.

The gradient ramp detection circuit 137, which provides a control signal to control circuit 135, may be integrated with the gradient system 118 by being installed in the gradient cabinet as a separate circuit or may be included as part of the functionality of the gradient system 118 itself. The ramp detection circuit 137 is connected to a real-time output of the gradient system 118, so that the detection circuit 137 can monitor application of gradient fields during a scan sequence and output a signal to the control circuit 135 causing it to interrupt or disconnect output of the patient monitoring electrodes whenever the gradient field is being ramped up or ramped down. As discussed above, it is the ramping stages of gradient field application which can cause induced voltages in ECG and EAM electrodes. Thus, during steady state "on" and fully "off" stages of gradient field application, the gradient ramp detection circuit 137 outputs a signal to the control circuit 135 causing it to connect or communicate the output of the patient monitoring electrodes to the processor 130.

Likewise, the RF system 120 may also be connected to, or include, a detection circuit (not shown), but control of signal gating control circuit 135 according to operation of the RF system may simply be achieved using existing output lines of the RF system. For example, in many MRI systems, an unblank signal is output by the RF amplifier of the RF system 120 just prior to and/or during RF transmission which could also be used for control of the control circuit 135.

Alternatively, the signal gating control circuit 135 may be responsive to signals from the scan prescription workstation 102, or the pulse sequence server 110 that indicate when the gradient system will be ramping up or down and/or when the RF system will be transmitting. The control circuit 135 may also be responsive to the presence of other noise-causing signals that are related to or accompany the operation of the gradient and/or RF system. For example, in certain GE MRI scanners, a 1000V signal is sent to the RF body coil to reverse bias the diodes on it, prior to the actual RF signal being sent from the RF amplifier. This 1000V signal can also create substantial noise within the bore of the magnet, such as in ECG and EAM electrodes, so the control circuit 135 can also disconnect output from such electrodes during application of the 1000V signal. In addition, the control circuit 135 may also be responsive to a simple user override. Furthermore, as stated above, the control circuit 135 may also gate the output of other physiological monitoring tools, such as pulse oximeters, blood pressure cuffs, respiratory monitors, and the like, which may also experience induced voltages and noise from gradient and RF operation during an MR scan.

Once the gated output of the ECG or EAM electrodes reaches the processor 130, the processor 130 then communicates the gated ECG or EAM information to the pulse sequence server 110 and/or workstation display 104. Thus, the gated information can be used for displaying an ECG trace or an EAM image, as will be described in more detail below, and for MR image acquisition. That is, for cardiac-gated scans, pulse sequence server 110 can synchronize, or "gate," the performance of the scan with the subject's heart beat or respiration. In other embodiments, the control circuit 135 may communicate ECG signals directly to the pulse sequence server 110 instead of, or in addition to, communication to the processor 130.

Figure 2:
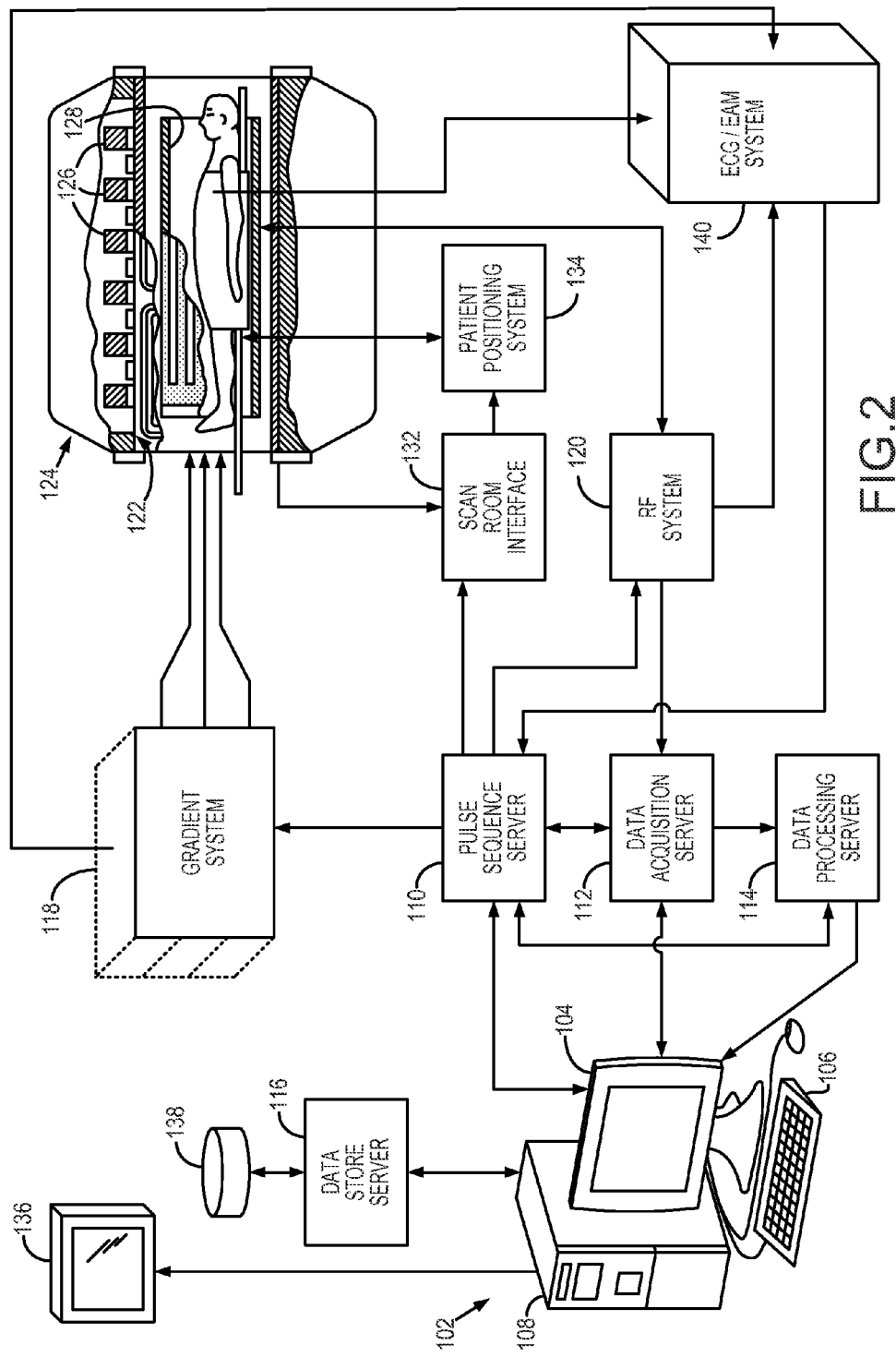
FIG. 2 is a block diagram of an exemplary magnetic resonance imaging ("MRI") system employed in combination with an exemplary ECG/EAM system in accordance with the present invention.

Referring now to FIG. 2, an additional embodiment is shown in which a separate, stand-alone ECG or EAM system 140 is employed in conjunction with a standard MRI system. The stand-alone system 140 may include, for example, a portable ECG unit offered by such companies as GE Healthcare, Cardiac Science, Medrad, and Invivo. Using this arrangement, patient monitoring can seamlessly continue (1) outside of, and apart from, the MRI system, (2) inside the MRI system when no scanning is taking place, and (3) inside the MRI system during an MRI scanning sequence. In this embodiment, the gradient ramp detection circuit, the ECG/EAM signal gating control circuit, and the ECG/EAM receiver or processor are all integrated into the stand-alone system 140.

During operation, the ECG/EAM system 140 is connected via an MRI scanner interface to output lines of the gradient system 118 and the RF system 120, to allow the internal gradient ramp detection circuit and signal gating control circuit to prevent or disregard ECG/EAM acquisition at the proper times. Thus, within the stand-alone ECG or EAM system 140, a chip or circuit may be included for detecting periods of gradient ramping in real time and sending control signals to a signal gating control switch or circuit that connects or disconnects ECG/EAM acquisition in coordination with the detected periods of gradient ramping. Likewise, a chip or circuit may be included for detecting periods of RF transmission, or receiving signals indicating that RF transmission is taking place or about to take place, in real time, and sending control signals to a signal gating control switch or circuit that connects or disconnects ECG/EAM acquisition in coordination with the periods of RF transmission. Alternatively, the ECG/EAM system 140 may include software that allows the system to receive input regarding operation of the gradient system 118 and RF system 120, calculate periods of gradient ramping and/or RF transmission, then ignore output from the ECG/EAM electrodes during those periods. In either case, the MRI system may be adapted or retrofit to include simple, removable connection points for plug-in leads so that the signals regarding operation of the gradient system 118 and RF system 120 may be communicated to the ECG/EAM system 140. Alternatively, the ECG/EAM system 140 may simply be connected to the pulse sequence server 110 or workstation 104 to receive information concerning the pulse sequence prescriptions for the gradient and RF systems.

Figure 3:
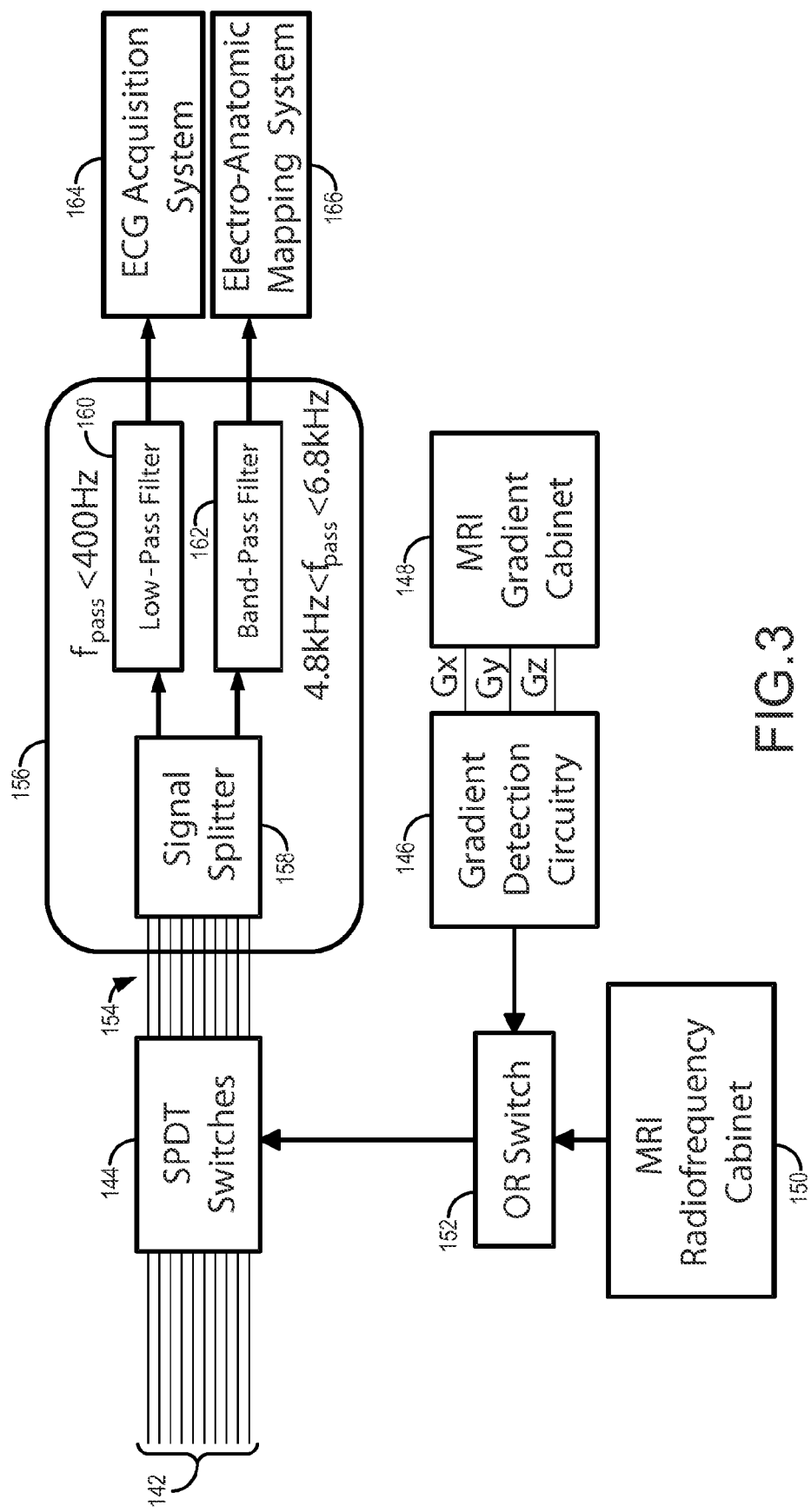
FIG. 3 is a block diagram of a representative ECG/EAM switching and processing circuit in accordance with the present invention.
Figure 4A:
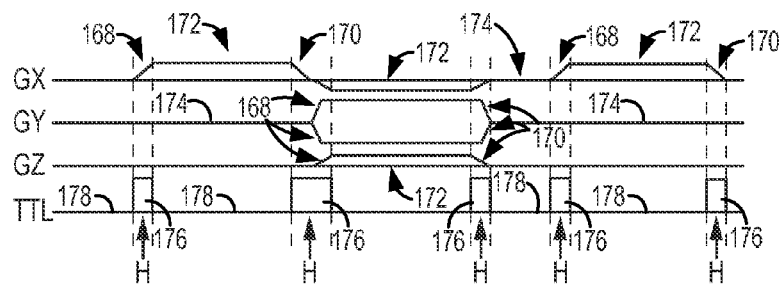
FIGS. 4A-4E is a chart depicting gradient waveforms from an exemplary MRI scan and exemplary ECG traces.
Figure 4B:
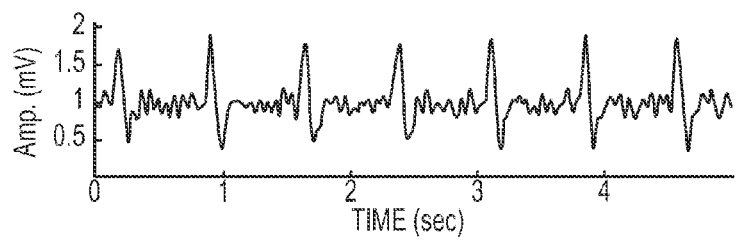
Figure 4C:
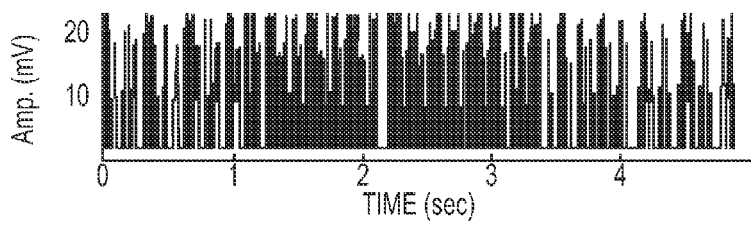
Figure 4D:
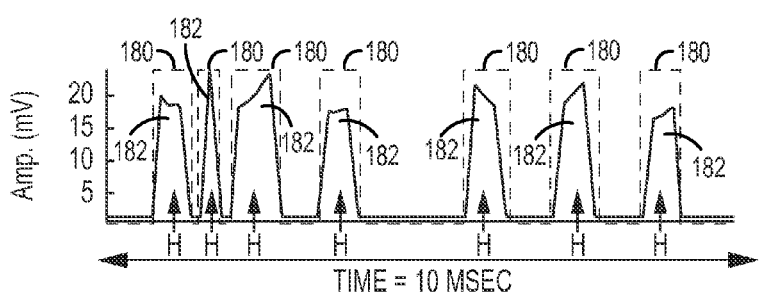
Figure 4E:
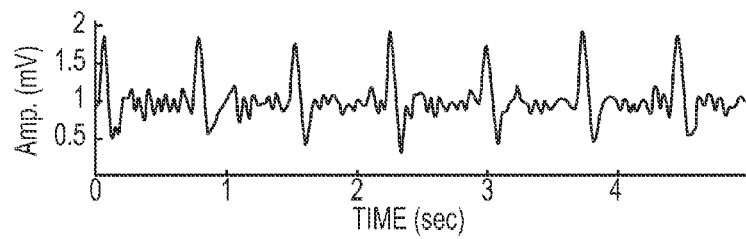

Referring now to FIG. 3, a functional block diagram is shown, which depicts the operation and interconnection of certain aspects of the above-described embodiments in greater detail. In FIG. 3, a plurality of leads 142 from a set of ECG or EAM electrodes and/or associated catheters (not shown) extend to one or more signal gating control circuits 144. For ECG-only systems, these lines will contain ECG signals, which generally are on the order of a few milli-volts at a few hundred Hz. For EAM systems, these lines may contain ECG signals as well as positional signals at a few kHz.

As discussed above, single pole double throw (SPDT) switches may be used to gate the communication of the electrodes' output. In the embodiment depicted in FIG. 3, the switches 144 are responsive to control signals from the MRI RF system 150 and the MRI gradient system 148. (However, as discussed above, a software or signal processing approach may be taken in lieu of, or even in combination with, a switch, to disregard physiological condition acquisition during periods of induced noise.) A gradient detection circuit 146 is employed to monitor gradient waveforms output by the gradient system 148 in real time to determine periods when gradient fields in the X, Y, or Z direction are being ramped up or ramped down. Thus, a circuit 152 may be used to perform an "OR" function, allowing the switches to be disconnected whenever gradient ramping is occurring OR when RF transmission is occurring. This "OR" circuit 152 may be integrated with the switching circuits 144 and/or both circuits may be integrated into a stand-alone ECG or EAM system. As discussed above, however, an "OR" functionality is not necessarily required, since embodiments of the invention may gate electrode output according to only one noise-inducing MR function (e.g., gating according to only gradient ramping, according to only RF transmission, or according to only some other MR function like 1000V diode biasing signals).

Upstream of the switching circuits 144, the gated electrode outputs 154 are communicated to a receiver or processor 156 during periods of the MRI scan sequence at which no gradient fields are being ramped up or down (i.e., all X, Y, and Z gradients are either at a steady state "on" or are fully "off") and/or no RF transmission is taking place. Thus, the switching circuits 144 (or, in other embodiments, a signal gating software algorithm or digital signal processing circuit) prevent the processor 156 from using output of the ECG or EAM electrodes that was affected by noise caused by induced voltages.

In an EAM system, as shown, the receiver/processor 156 includes a signal splitter 158 to split each gated electrode output 154. One of the split signals for each gated electrode output 154 is then sent through a low-pass filter 160 to separate out the ECG component of the electrode output 154, while the other split signal is sent through a band-pass filter 162 to separate out the EAM positional component of the electrode output 154. In an ECG-only system, though a signal splitter 158 is not necessary, it may be still be desirable to use a low pass filter 160 to reduce stray noise, for example a minimum-phase low pass Butterworth filer. These filtering steps may be performed digitally in either a workstation or in the processing unit of an ECG/EAM unit (such as a GE Cardiolab unit).

The receiver/processor 156 also includes, or is connected to, an ECG acquisition system 164 and/or an EAM system 166. Because the electrodes' output has been gated in coordination with operation of the gradient system 148 and RF system 150, the output that is communicated to receiver/processor 156 and associated circuitry 164, 166 does not include gradient-induced noise. Accordingly, an ECG acquisition system 164 (such as a Cardiolab system) can sample only gradient and RF noise-free ECG signals, and display physiological monitoring-quality images of ECG traces. These images may be displayed on a screen of a stand-alone ECG unit, on the screen of an MRI system workstation, or both. Likewise, an EAM system 166 can sample only gradient and RF noise-free EAM positional signals, and can thus display full electrophysiological images without distortion or complication from gradient or RF noise. Correspondingly, because the output of the ECG/EAM electrodes is gated so as to reduce the effect of induced voltages, a full set of electrodes can be utilized in a normal monitoring arrangement, such as, for example, a standard 12-lead electrode arrangement. In other words, there is no longer a need to reduce the number of electrodes or the spacing of the electrodes to attempt to limit the amount of induced noise, because the periods of acquisition in which noise is induced by gradient ramping or RF transmission are gated or ignored.

In addition to preventing induced voltages in electrode outputs from affecting image quality, the switches 144 can also be used for another purpose in EAM systems. During operation of an EAM system, some electrodes are used to transmit electric signals that are detected and sampled by electrodes in interventional catheters located inside a patient anatomy, such as a heart chamber. Because the transmission and reception of these electric signals can experience interference from the gradient and RF transmissions inside an MRI scanner, the switches 144 can also be used to prevent electrodes from transmitting during a gradient ramping period or an RF transmission period. In this case, the switches 144 would be gated according to the same control signals, and would still be connected to electrode leads, but the transmission of signals on the leads would be travelling in the opposite direction—to the patient from the receiver/processor 156, rather than from the patient to the receiver/processor 156. Likewise, preventing transmission of electric signals from EAM electrodes during certain portions of an MRI scan sequence also reduces the risk that the electric signals from the EAM electrodes could be picked up by the RF coil of the MRI scanner and affect image data acquisition of the MRI system.

Referring now to FIG. 4, a set of graphs 4A-4E of exemplary gradient waveforms and ECG signals is depicted to illustrate certain aspects of the invention. Graph 4A shows a set of waveforms Gx, Gy, and Gz representing the timing and amplitude of gradient fields applied in the X, Y, and Z directions inside an MRI scanner during a scan sequence. As can be seen, the gradients are usually applied such that they have trapezoidal waveforms, with periods of ramping up 168 and periods of ramping down 170 between steady state "on" periods 172 and fully "off" periods 174. The bottom line of graph 4A depicts a exemplary "TTL" control signal which experiences a high level 176 whenever a gradient field in any direction is ramping up or ramping down, and a low level 178 at all other times. This control signal represents the output of a gradient ramping detection circuit, as described above, which is used to cause a signal gating switch to open (high levels 178) and close (low levels 178) according to the gradient ramping waveforms.

Graph 4B is an exemplary ECG signal acquired when no MRI scan sequence is taking place. Graph 4C, in contrast, is an exemplary ECG signal acquired during an MRI scan, with no gating or other approach to compensate for induced voltages in the ECG electrodes. Graph 4D is a close-up view of a segment of FIG. 4C, with an exemplary TTL control signal (Graph 4A) superimposed thereon. As can be seen, periods 180 when gradient ramping is taken place (as identified by high TTL levels "H") cause false spikes 182 to be seen in the ECG signal.

Graph 4E is an exemplary ECG signal acquired during an MRI scan sequence, using the gradient gating aspects of the invention described above. As can be seen, especially in comparison to Graph 4C, the ECG signal is far less affected by induced voltages, and is of a quality that can be easily used for normal physiological monitoring (e.g., the QRS points of the ECG trace can be accurately and easily determined).

Further localization system embodiments described below provide noise tolerant operation in noise-inducing environments, for example, in magnetic resonance imaging (MRI) environments. The embodiments described below in particular relate to impedance-based Electro-Anatomical Mapping systems which include localization or positioning functionality (e.g., EnSite™ NavX™ "Classic" and Ensite™ NavX™ Velocity™ systems), which output among other things device electrode position data that can be used for catheter tracking, geometry construction and the like. The embodiments described below include functionality that implements various noise mitigation strategies for those signals used to determine catheter (electrode) position. It should be understood, however, that such approaches, while useful for extending such EAM system's capabilities in an MRI or other noisy environments, are not necessarily exclusive. That is, the strategies described below may be used either alone or in combination with not only other noise mitigation strategies (e.g., mitigations related to ECG and electrogram measurements described above), but with other MRI-compatibility enhancing strategies (e.g., mitigation strategies to address MRI heating effects, and/or MR image distortion effects).

While the embodiments described above in connection with FIGS. 1-4, involving front-end switches and filters, can work for ECG and electrogram ("Egram") signals, they have disadvantages for noise mitigation of catheter tracking signals, at least as such tracking signals are currently implemented in commercial embodiments of impedance-based EAM systems, such as EnSite™ NavX™ Classic and Ensite™ NavX™ Velocity™. The blanking and filtering functions described above can work well as long as the blanking intervals are relatively short in duration with respect to changes in the signal of interest. This condition can be met for ECG and Egram signals where the frequencies of interest are mostly below 50 Hz and are almost entirely below 500 Hz. Occasional blanking pulses lasting up to several milliseconds in duration will affect the partially-blanked resulting signal, but the effects are generally minor and clinically acceptable. The impedance signals used for electrode tracking in general (e.g., in the NavX™ system) have three properties which work against the kind of simple blanking described in connection with FIGS. 1-4E.

First, the raw signals are in the range of 5-8 kHz so that if the blanking is to have no significant effect on the raw 5-8 kHz waveform then the acceptable (maximum) blanking intervals are probably on the order of microseconds, rather than milliseconds. Second, the impedance measurements as currently implemented in the NavX™ system are time-multiplexed into discrete time intervals of approximately 0.5 msec to 1 msec in duration (depending on Velocity™/Classic platform). At the boundary of each time-slice, the signal is abruptly discontinuous and so any low-pass filtering done after the blanking switches would tend to smear the signal from one time-slice into the next time-slice. An analog delay line could be used to correct for the low-pass filter delay, but analog delay lines cannot be made perfect and the large discontinuities in the impedance signal at the time-slice boundaries will not be perfectly preserved and will introduce some error. Third, the signals are synchronously demodulated against a 5-8 kHz reference signal and then integrated with an integrator which is re-set at the beginning of each time-slice. The low-pass filtering and analog delay line would likely change the phase of the signal and require re-calibration of the synchronous demodulator, and any intervals during which the signal is blanked to zero would reduce the amplitude of the integrated signal, introducing an un-recoverable error.

While in one contemplated embodiment, the impedance-based EAM system employs continuous-time synchronous demodulation, in which case all the above problems are more manageable (and in that case the simple front-end switches would be more feasible), there nonetheless exists a need to address the above problems for current implementations. Before proceeding to a description of the specific noise mitigation embodiments, however, a brief overview for context of an exemplary electrical impedance-based EAM system will be set forth.

Figure 5:
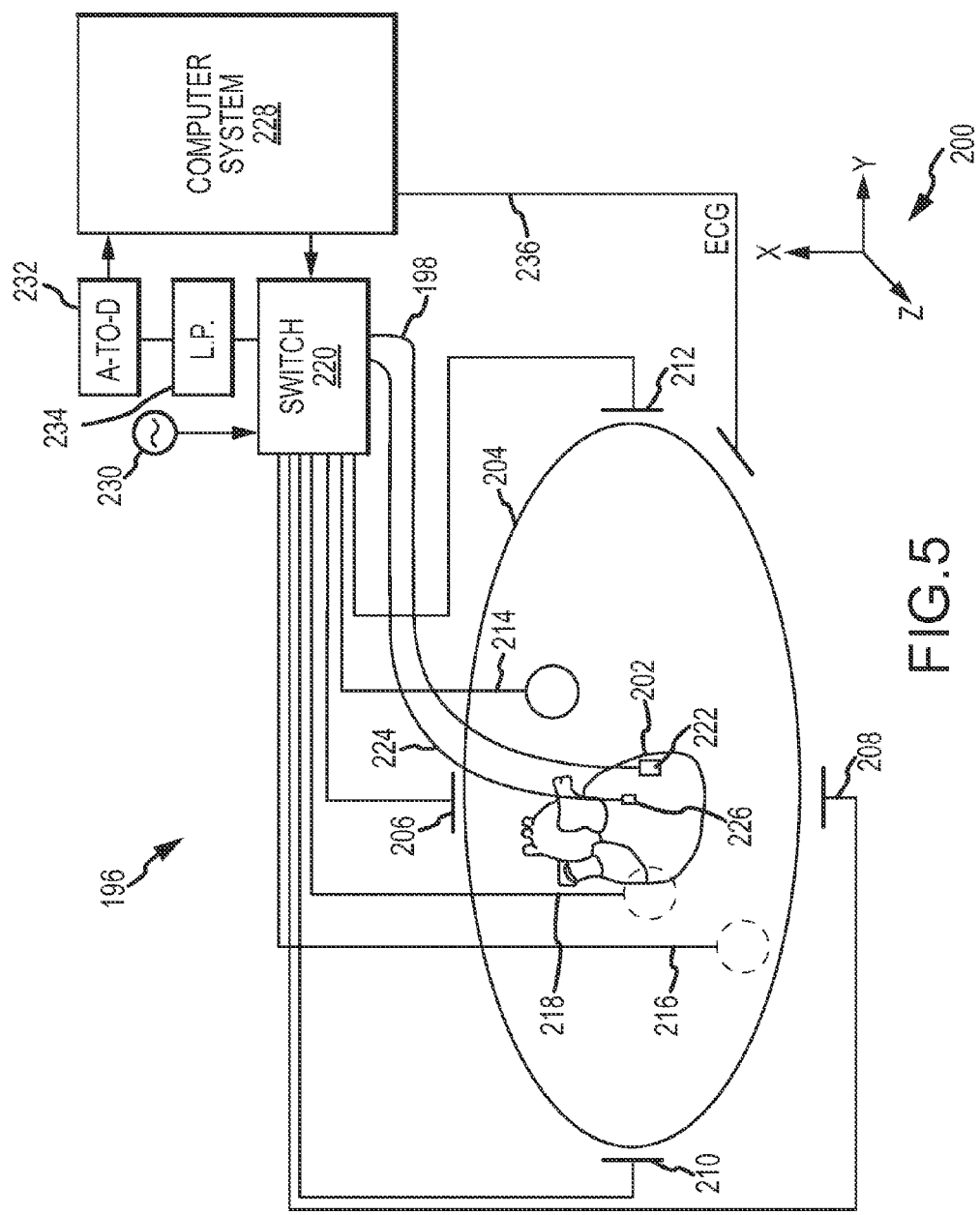
FIG. 5 is a diagrammatic and block diagram view showing, in an embodiment, an exemplary electrical impedance-based positioning system.
Figure 6A:
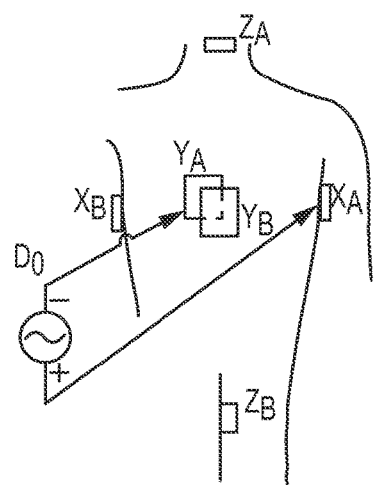
FIGS. 6A-6D are schematic diagrams of exemplary dipole pairs of driven body surface electrodes.
Figure 6B:
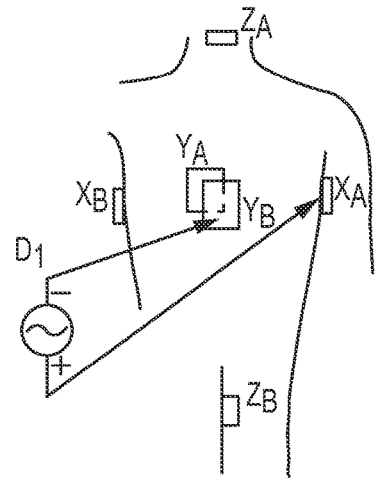
Figure 6C:
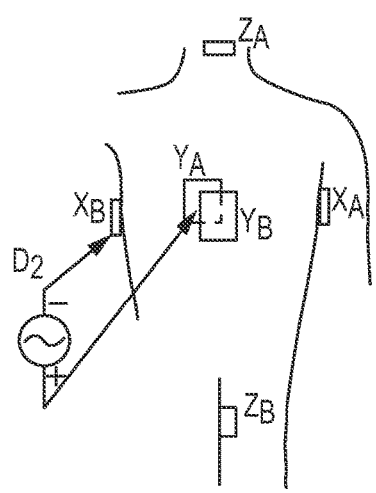
Figure 6D:
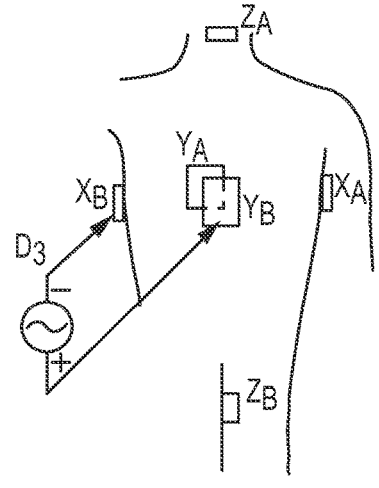

FIG. 5 is a simplified schematic and block diagram of an impedance-based Electro-Anatomical Mapping system 196 configured to, among other things, determine at least a position of a medical device 198 (e.g., catheter) in a reference coordinate system 200. System 196 may comprise various visualization, mapping and navigation components as known in the art, including, for example, an EnSite™ NavX™ Electro Anatomical Mapping System commercially available from St. Jude Medical, Inc., or as seen generally by reference to U.S. Pat. No. 7,263,397 (the '397 patent), or U.S. Patent Publication No. 2007/0060833 A1, U.S. application Ser. No. 11/227,580 filed 15 Sep. 2005 (the '580 application). The '397 patent and the '580 application are both hereby incorporated by reference as though fully set forth herein.

System 196 includes a diagrammatic depiction of a heart 202 of a patient 204. The system includes the ability to determine a catheter electrode location (i.e., position and orientation) as the catheter distal end is moved around and within a chamber of the heart 202. For this purpose, three sets of body surface electrodes (patches) are shown: (1) electrodes 206, 208 (X-axis); (2) electrodes 210, 212 (Y-axis); and (3) electrodes 214, 216 (Z-axis). Additionally, a body surface electrode ("belly patch") 218 is shown diagrammatically. The surface electrodes are all connected to a switch 220. Of course, other surface electrode configurations and combinations are suitable for use with the present invention, including fewer electrodes, e.g., three electrodes, more electrodes, e.g., twelve, or different physical arrangements, e.g., linear arrangement instead of an orthogonal arrangement.

Device 198 is shown as a catheter with a distal electrode 222. Catheter 196 may have additional electrodes in addition to electrode 222 (e.g., a catheter tip electrode and/or ring electrodes). FIG. 5 also shows a second, independent catheter 224 with a fixed reference electrode 226, which may be stationary on the heart for calibration purposes. In many instances, a coronary sinus electrode or other fixed reference electrode 226 in the heart 202 can be used as a reference for measuring voltages and displacements.

It should be understood that catheter 198 may include still other electrodes, and in other embodiments, such as in EP or RF ablation embodiments, the other electrodes may be used for any number of diagnostic and/or therapeutic purposes. For instance, such electrodes and therefore such catheters may be used for performing ablation procedures, cardiac mapping, electrophysiological (EP) studies and other diagnostic and/or therapeutic procedures. Embodiments are not limited to any one type of catheter or catheter-based system or procedure.

FIG. 5 further shows a computer system 228, a signal generator 230, an analog-to-digital converter (ADC) 232 and a low-pass filter 234. Computer system 228 includes a processing apparatus configured to perform many of the functions and operations described herein. Computer system 228 may be configured to control signal generator 230 in accordance with predetermined strategies to selectively energize or drive various pairs (dipoles) of surface electrodes (patch pairs), as described in greater detail below. In operation, computer system 228 may obtain or acquire via filter 234 and A-to-D converter 232 (1) electrode measurements (i.e., voltage readings) of tracked electrodes; (2) raw patch data (i.e., voltage readings). In addition, system 228 is configured to use at least the electrode measurements, and in an embodiment, the raw patch data to determine the raw, uncompensated, electrode location coordinates of a catheter electrode positioned inside the heart or chamber thereof (e.g., such as electrode 222) in three-dimensional coordinate system 200.

Computer system 228 may be further configured to perform one or more compensation and adjustment functions, and to output a location in coordinate system 200 of one or more electrodes such as electrode 222. Motion compensation may include, for example, compensation for respiration-induced patient body movement, as described in U.S. application Ser. No. 12/980,515 (the '515 application), which is hereby incorporated by reference as though fully set forth herein.

In an embodiment, most or all of the conventional twelve (12) ECG leads, may be coupled to body surface electrodes and designated collectively by reference numeral 236, may be provided to support the acquisition of an electrocardiogram (ECG) of the patient 204. As shown, ECG leads 236 (if provided) may be coupled directly to computer system 228 for acquisition and subsequent processing to obtain the phase of the heart in the cardiac cycle. ECG leads 236 may be also provided to other systems.

Each body surface (patch) electrode is independently coupled to switch 220 and pairs of electrodes are selected by software running on computer system 228, which couples the patches to signal generator 230. A pair of electrodes, for example, the Z-axis electrodes 214 and 216, may be excited by signal generator 230 to generate an electrical field in the body of patient 204 and heart 202. In one embodiment, this electrode excitation process occurs rapidly e.g., on the order of 100 times per second in an embodiment, and sequentially in a respective time slice as different sets of patch electrodes are selected and, in an embodiment, one or more of the unexcited surface electrodes are used to measure voltages, along with the resultant voltages on the tracked electrodes. Excitation of the particular pattern of patch pairs is repeated.

During the delivery of the excitation signal (e.g., current pulse), the remaining (unexcited) patch electrodes may be referenced to the belly patch 218 and the voltages impressed on these remaining electrodes are measured by the A-to-D converter 232. In this fashion, in an embodiment, the surface patch electrodes are divided into driven and non-driven electrode sets. Low pass filter 234 may process the voltage measurements. The filtered voltage measurements are transformed to digital data by analog to digital converter 232 and transmitted to computer 228 for storage under the direction of software. This collection of voltage measurements is referred to herein as the "patch data." The software has access to each individual voltage measurement made at each surface electrode during each excitation of each pair of surface electrodes.

The measurements made at electrode 222, along with the patch data, may be used to determine a relative location of electrode 222 in coordinate system 200. Potentials across each of the six orthogonal surface electrodes may be acquired for all samples except when a particular surface electrode pair is driven (in an embodiment). In one embodiment, sampling while a surface electrode acts as a source or sink in a driven pair is normally avoided as the potential measured at a driven electrode during this time may be skewed by the electrode impedance and the effects of high local current density. In an alternate embodiment, however, sampling may occur at all patches (even those being driven).

Generally, in one embodiment, three nominally orthogonal electric fields are generated by a series of driven and sensed electric dipoles in order to realize the localization function of the catheter in a biological conductor. Alternately, these orthogonal fields can be decomposed and any pair of surface electrodes (e.g., non-orthogonal) may be driven as dipoles to provide effective electrode triangulation.

FIGS. 6A-6D show a plurality of exemplary non-orthogonal dipoles, designated $D_0$, $D_1$, $D_2$ and $D_3$, set in coordinate system 200. In FIGS. 6A-6D, the X-axis surface electrodes are designated $X_A$ and $X_B$, the Y-axis surface electrodes are designated $Y_A$ and $Y_B$, and the Z-axis electrodes are designated $Z_A$ and $Z_B$. For any desired axis, the potentials measured across an intra-cardiac electrode 222 resulting from a predetermined set of drive (source-sink) configurations may be combined algebraically to yield the same effective potential as would be obtained by simply driving a uniform current along the orthogonal axes. Any two of the surface electrodes 206, 208, 210, 212, 214, 216 (see FIG. 5) may be selected as a dipole source and drain with respect to a ground reference, e.g., belly patch 218, while the unexcited body surface electrodes measure voltage with respect to the ground reference. The measurement electrode 222 placed in heart 202 is also exposed to the field from a current pulse and is measured with respect to ground, e.g., belly patch 218. In practice, a catheter or multiple catheters within the heart may contain multiple electrodes and each electrode potential may be measured separately. As previously noted, alternatively, at least one electrode may be fixed to the interior surface of the heart to form a fixed reference electrode 226, which may also be measured with respect to ground.

Data sets from each of the surface electrodes and the internal electrodes are all used to determine the location of measurement electrode 222 within heart 202. After the voltage measurements are made, a different pair of surface electrodes is excited by the current source and the voltage measurement process of the remaining patch electrodes and internal electrodes takes place. The sequence occurs rapidly. To a first approximation the voltage on the electrodes within the heart bears a linear relationship with position between the patch electrodes that establish the field within the heart, as more fully described in U.S. Pat. No. 7,263,397 referred to above. These voltage readings may be processed in connection with injected current values to obtain impedance measurements, consistent with, for example, U.S. Pat. No. 7,263,397 and other documents referred to herein.

The system described in connection with FIGS. 5-6 thus include means for selectively driving, during a respective time slice, an excitation signal across a respective one of a plurality of paired body surface electrodes. The driving means is controlled to repeat the excitation through a pattern (described above) of surface electrodes. The system also includes means for acquiring, during the time slices, a respective resultant (voltage) signal from one or more tracked, device electrodes. The system further includes means for determining, for each time slice, a respective impedance measurements based on at least a resultant signal.

Due to differences in the EnSite™ NavX™ Classic and EnSite™ NavX™ Velocity™ hardware platforms, different embodiments will be described addressing each target system.

Figure 7:
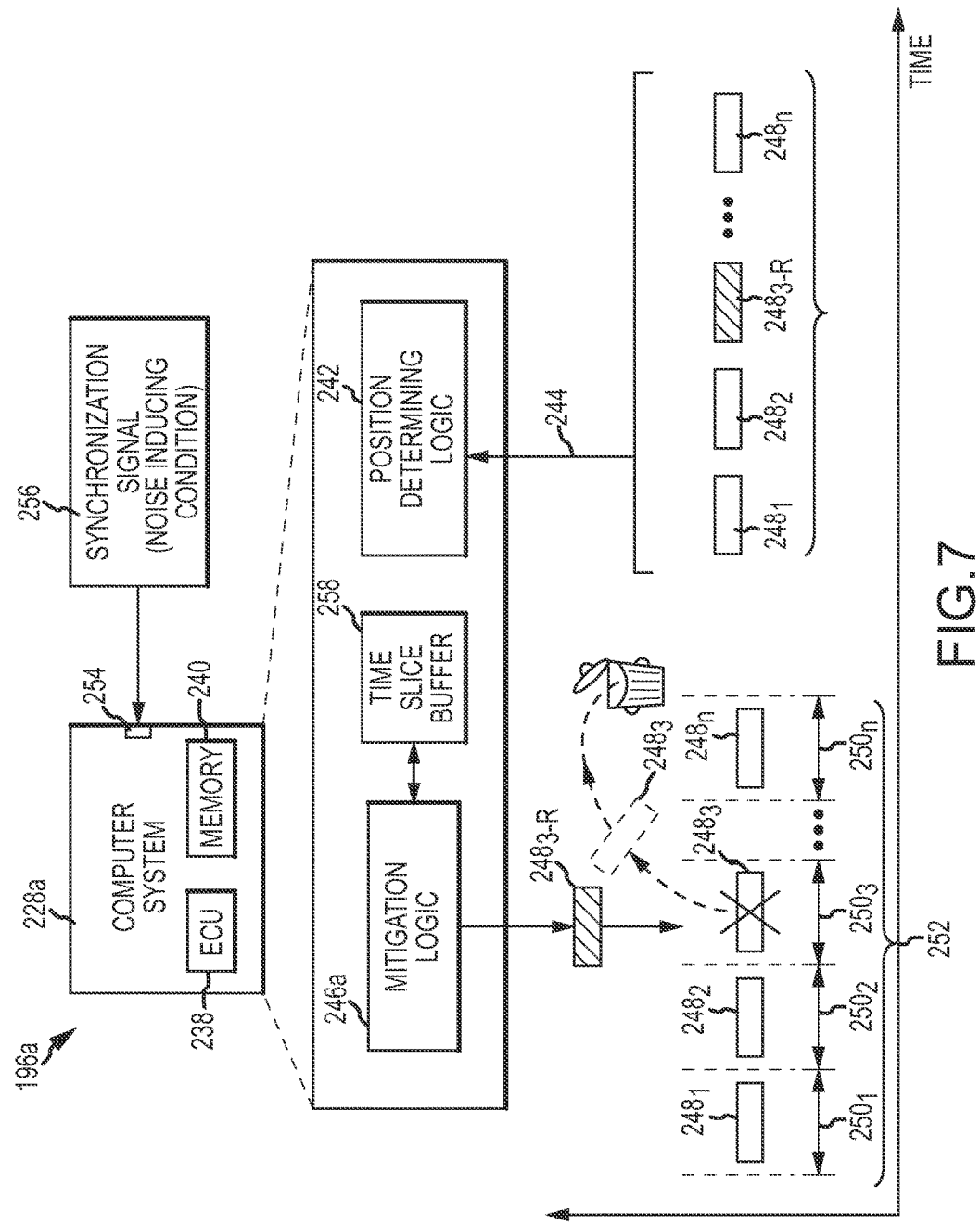
FIG. 7 is a diagrammatic and block diagram of a first embodiment of a noise-tolerant impedance-based EAM system with noise mitigation logic.

FIG. 7 is a diagrammatic and block diagram of an embodiment of a noise-tolerant impedance based EAM system, designated 196*a*. The system 196*a* includes a modified computer system, designated system 228*a*, which includes functionality for mitigating the adverse effects of externally induced noise. The system 228*a* includes an electronic control unit (ECU) 238 (including a programmable processor) and a computer-readable memory 240. The system 228*a* includes position determining logic 242, which is stored in the memory 240 and which is configured for execution by the ECU 238. The position determining logic 242 is configured to determine the position (and orientation) of one or more tracked electrodes based at least one a plurality of impedance measurements 244 taken with respect to the tracked electrode (e.g., electrode 222 in FIG. 5). System 196*a* provides for continuous positioning tracking, even where a patient is moved into and out of an MRI system imaging bore.

In accordance with an embodiment, the system 228*a* further includes mitigation logic 246*a*, which may also be stored in memory 240 and which is also configured for execution by the ECU 238. Mitigation logic 246*a* is configured to identify one or more impedance measurements taken by the system 196*a* during an external noise inducing condition and which are therefore subject to corruption. The mitigation logic 246*a* is thus further configured to replace or substitute the one or more impedance measurements in accordance with a predetermined mitigation strategy, described below.

In the system 196*a*, which may correspond to a commercially available system known as Ensite™ NavX™ (or now "Classic", to distinguish for Ensite™ NavX™ Velocity™, described below). In system 196*a*, a plurality of impedance samples, designated $248_1$, $248_2$, $248_3$, . . . , $248_n$, are obtained in respective, discrete time slices designated $250_1$, $250_2$, $250_3$, . . . , $250_n$. In a constructed embodiment, each time slice is 1/1200 second in duration, or approximately 830 microseconds. During each time slice, an excitation signal (e.g., a burst of ~5.68 kHz electrical current) is driven between two of the six NavX™ body surface electrodes ("patches") (see FIGS. 5 and 6A-6D), and the resultant signal (i.e., voltage) is measured on each tracked electrode (up to 64 electrodes simultaneously). In an embodiment, measurements are obtained using thirteen different pairs of NavX patches ("paired body surface electrodes") in sequence, then the pattern, designated as pattern 252, is repeated. The signal measured on a given electrode when driving current through a given pair of NavX patches is completely independent of the signal measured on the same electrode when driving current through a different pair of NavX patches. Hence each time-slice represents a measurement which is completely independent (and discontinuous) with respect to the preceding time-slice.

System 228*a* may be configured with an input port 254 configured to receive a synchronization signal 256. In an embodiment utilizing the so-called Classic platform of Ensite™ NavX™, such input port 254 may be available as a stimulation input or a 'stim input', which can be used to receive the synchronization signal. The system 228*a* is further configured to respond to changes in state of the synchronization signal 256 and provide an internally-available synchronization parameter whose logic state corresponds to whether the synchronization signal 256 is asserted (or de-asserted). It should be understood, however, that the commercially available Ensite™ NavX™ Classic system, which has such a "stim" input, was not configured to use this mechanism as will be described below.

The synchronization signal 256 indicates whether a potentially noise-inducing condition exists (or not). For example, the MR system described above in connection with FIGS. 1-4E can provide a TTL-level signal indicating that noise-inducing events are about to occur (i.e., magnet gradient ramps, RF pulse and the like). In an embodiment, this TTL-level signal may be provided to input 254 whenever an MR-generated noise pulse is imminent, and an input amplifier passes along the "stim" input to the mitigation logic 246*a*.

The mitigation logic 246*a* is configured to monitor the logic state of the internal synchronization parameter and thus becomes aware, when the synchronization signal 256 is asserted, that one or more corresponding impedance signals, such as one or more of the impedance measurements $248_1$, $248_2$, $248_3$, . . . , $248_n$, are subject to corruption by noise. In a preferred embodiment, the predetermined mitigation strategy is to replace the corrupted impedance measurement with a previously-obtained impedance measurement associated with the same patch pair associated with the corrupted impedance measurement. In an embodiment, the previously-obtained impedance measurement is taken from the immediately previous pattern (i.e., from one of the immediately taken thirteen time-slices). In this regard, the mitigation logic 246*a* may maintain a time slice buffer 258 that contains impedance measurements from the immediately preceding cycle or pattern of patch pair excitation activity.

For example, assume that mitigation logic 246*a* determines that time slice $250_3$ will be subject to corruption by noise, for example, by timely assertion of the synchronization signal 256 by the MR system, as described above. The mitigation logic 246*a* will discard or ignore impedance measurement $248_3$, and replace it with impedance measurement $248_{3\text{-}R}$. Impedance measurement $248_{3\text{-}R}$ is available from memory 258 and is associated with the same patch pair/time slice $250_3$ but from the immediately preceding pattern 252 of excitation or measurement activity. Once mitigation logic 246a has made this substitution, the composite plurality of impedance measurements 244, comprising impedance measurements $248_1$, $248_2$, $248_{3-R}$, . . . , $248_n$, are used by position determining logic 242 to determine the electrode position. It should be understood that if the same or a previous noise-inducing condition had corrupted the impedance measurement associated with time-slice $250_3$ in a previous pattern 252, that the mitigation logic 246a would have already made a replacement for that time slice.

Figure 8:
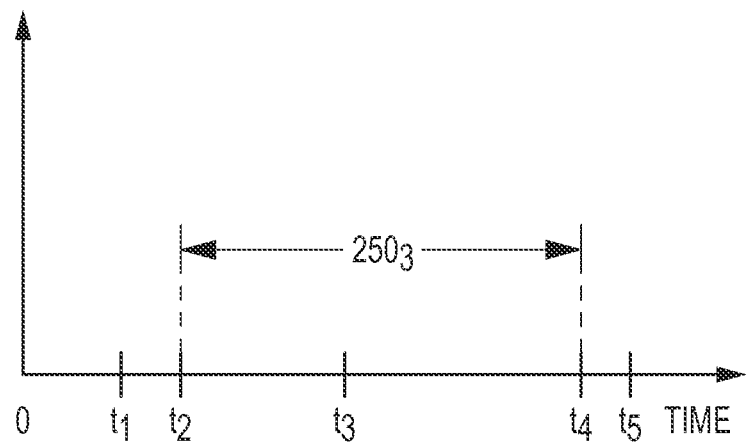
FIG. 8 is a timing diagram showing detection modes for detecting noise-inducing conditions.

FIG. 8 is timing diagram showing an exemplary time-slice $250_3$ with several possible detection timings related thereto. The mitigation logic 246a is configured to determine the time that the synchronization signal 256 is asserted and carry out the predetermined mitigation strategy based on such determined time. FIG. 8 shows an exemplary time-slice $250_3$ and several possible detection or recognition times designated $t_1$, $t_2$, $t_3$, $t_4$ and $t_5$. Due to the above-noted monitoring, the mitigation logic 246a may detect that the synchronization signal 256 has be asserted at time $t_1$, in anticipation of the occurrence of the noise-inducing condition. In this situation, the logic 246a can fetch the replacement impedance measurement $248_{3-R}$ forthwith and substitute it into the stream 244 of impedance measurements. However, in an embodiment, mitigation logic 246a can be further configured to buffer several time-slices of impedance data so that the synchronization signal 246a (e.g., the TTL-level signal mentioned above produced by the MR system) does not need to anticipate the MR-generated noise pulse—the TTL-level signal can precede the noise pulse, or be simultaneous with it (e.g., times $t_2$, $t_3$ or $t_4$), or even lag it (e.g., time $t_5$) if necessary. The necessary time-shift to align the synchronization signal (i.e., the TTL-level signal) with the corrupted impedance sample (time-slice) can be accomplished in software. The foregoing feature in effect relaxes the criticality of rapid noise-inducing condition detection/recognition, since the mitigation logic 246a is configured to detect and replace (as described above), even after a corrupted impedance measurement has been captured, but before it is sent on to the position determining logic 242. The feature allows the mitigation logic to "wait and see", i.e., hold data for up to some predetermined maximum time to determine whether any external noise-inducing conditions occurred.

It should be understood that system 196a is not limited to noise-tolerance in connection with MRI systems. In a variation, system 196a can be configured to provide noise tolerant operation when used in connection with a magnetic field-based positioning system, which may also include noise-inducing conditions (i.e., when electromagnetic field generators are activated, for example, the MediGuide™ system from MediGuide Ltd. of Haifa, Israel (now owned by St. Jude Medical, Inc.), and as generally shown with reference to one or more of U.S. Pat. No. 6,233,476 (the '476 patent), U.S. Pat. No. 7,197,354 (the '354 patent), and U.S. Pat. No. 7,386,339 (the '339 patent. The '476 patent, the '354 patent and the '339 patent are all hereby incorporated by reference as though fully set forth herein). System 196a can also be configured for noise-tolerant operation when used in connection with other variants which employ magnetic field generator operation (and thus noise-inducing conditions), at least in part, such as a combination magnetic field- and current-based system such as the CARTO 3™ System (with current- and magnetically-driven or receptive electrodes) available from Biosense Webster, and as generally shown with reference to one or more of U.S. Pat. No. 6,498,944 (the '944 patent), U.S. Pat. No. 6,788,967 (the '967 patent), and U.S. Pat. No. 6,690,963 (the '963 patent). The '944 patent, the '967 patent and the '963 patent are all hereby incorporated by reference as though fully set forth herein. In a further variation, the EAM system is based, at least in part, on magnetic-field positioning technology that includes sensing coils (e.g., as per the MediGuide™ system or the CARTO or CARTO 3 system), and where the mitigation logic operates to identify and replace position indicative readings from the sensing coils that may be corrupted by virtue of the noise inducing conditions originating with the MRI system (as described above).

Figure 9:
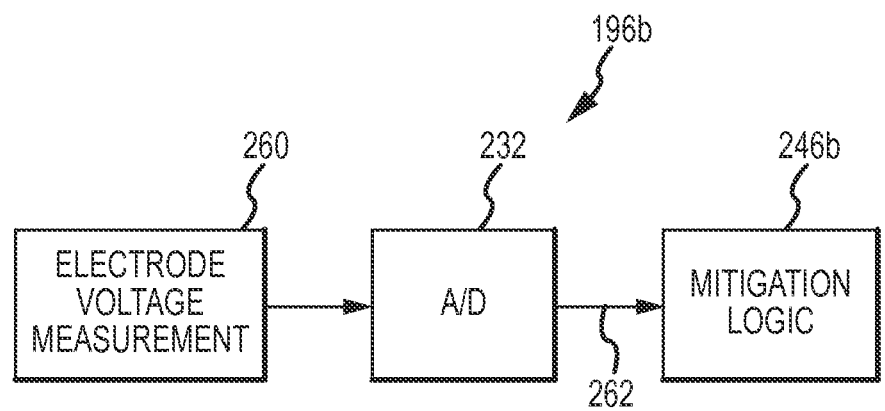
FIG. 9 is a block diagram of a second embodiment of a noise-tolerant impedance-based EAM system with noise mitigation logic.

FIG. 9 is a partial block diagram view of a second embodiment of noise-tolerant EAM system, designated system 196b. Unless otherwise stated, system 196b can be the same as system 196a. The system 196b includes a further embodiment of mitigation logic, designated mitigation logic 246b. In an embodiment, the system 196b may be based on a commercially available impedance-based EAM system, for example, the Ensite™ NavX™ Velocity™ platform described above. The basic operation of NavX™ on the Velocity™ platform is similar to the operation on the Classic platform, except that the time-slices are 500 microseconds in duration (in an embodiment) rather than 830 microseconds, the patch pair pattern repeats after 10 time-slices rather than 13 time slices, the excitation signal may be a current bursts using a frequency of ~8 kHz rather than ~5.68 kHz, and there are 132 available channels rather than 64 channels. Another difference is that while the measured signal (i.e., voltage reading taken from the tracked electrode) is synchronously demodulated in the analog domain in the Classic system, this function is done in the digital domain (i.e. after A/D conversion) in the Velocity™ system. This last difference is most significant and leads to a new way to deal with noise as described below.

In addition, the Velocity™ platform does not include a 'stim input' as described above in connection with FIG. 7 and so that mechanism for synchronization as described above is not available in system 196b. However, since the impedance signal is digitized BEFORE synchronous demodulation, any significant noise pulses can be detected via a software threshold comparison implemented in mitigation logic 246b immediately after A/D conversion. As shown in block diagram form, an electrode voltage measurement 260 is sampled by ADC 232 (also shown FIG. 5) to produce a corresponding digital signal 262.

Figure 10:
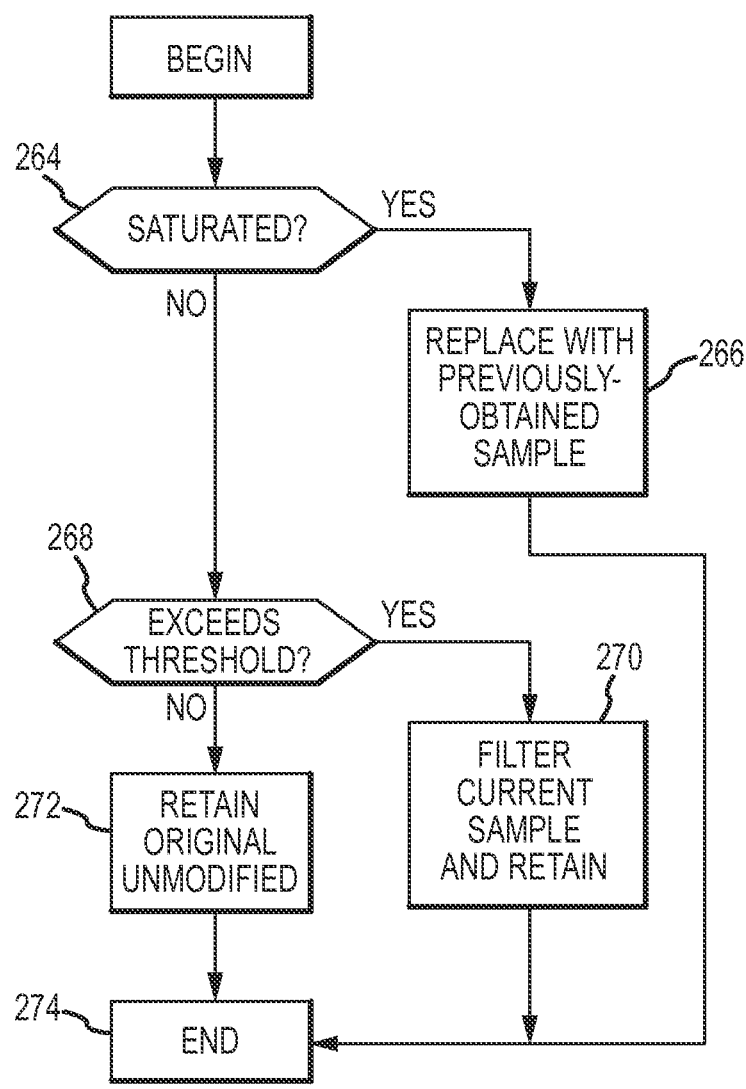
FIG. 10 is a flowchart showing a threshold-based detection method incorporated into the noise mitigation logic of FIG. 9.

FIG. 10 is a flowchart showing the processing that occurs through the execution of mitigation logic 246b. To begin, the mitigation logic 246b (in step 264) includes a mechanism to determine whether the ADC 232 input has been saturated, indicating that a significant noise pulse occurred and has corrupted the measurement. If the answer is "YES", then the method branches to step 266.

In step 266, the mitigation logic 246b replaces the digital signal 262 with a digital sample taken or measured during the immediately preceding cycle or pattern of excitation activity (i.e., the sample acquired 10 time-slices previous, in the described embodiment). The mitigation logic 246 is then configured to insert the replacement sample into the data stream, which is then handled (demodulated) in accordance with normal processing. However, if the answer in step 264 is "NO", then the method proceeds to step 268.

In step 268, mitigation logic 246b (which includes a mechanism to determine whether the resultant signal exceeds a threshold), determines whether the digital sample 262, while not saturated, nonetheless still exceeds some predetermined threshold indicating the presence of noise. If the answer is "YES", then the method proceeds to step 270, where logic 246b removes noise from the digital signal. For example, the mitigation logic 246b, in an embodiment, includes digital filters which are configured to be reasonably effective and which reduce the level of interference to acceptable levels. If the answer in step 268 is "NO", then the method branches to step 272.

In step 272, the mitigation logic 246b observes normal levels, and thus no modification of the digital sample 262 is needed. The method ends in step 274.

Figure 11:
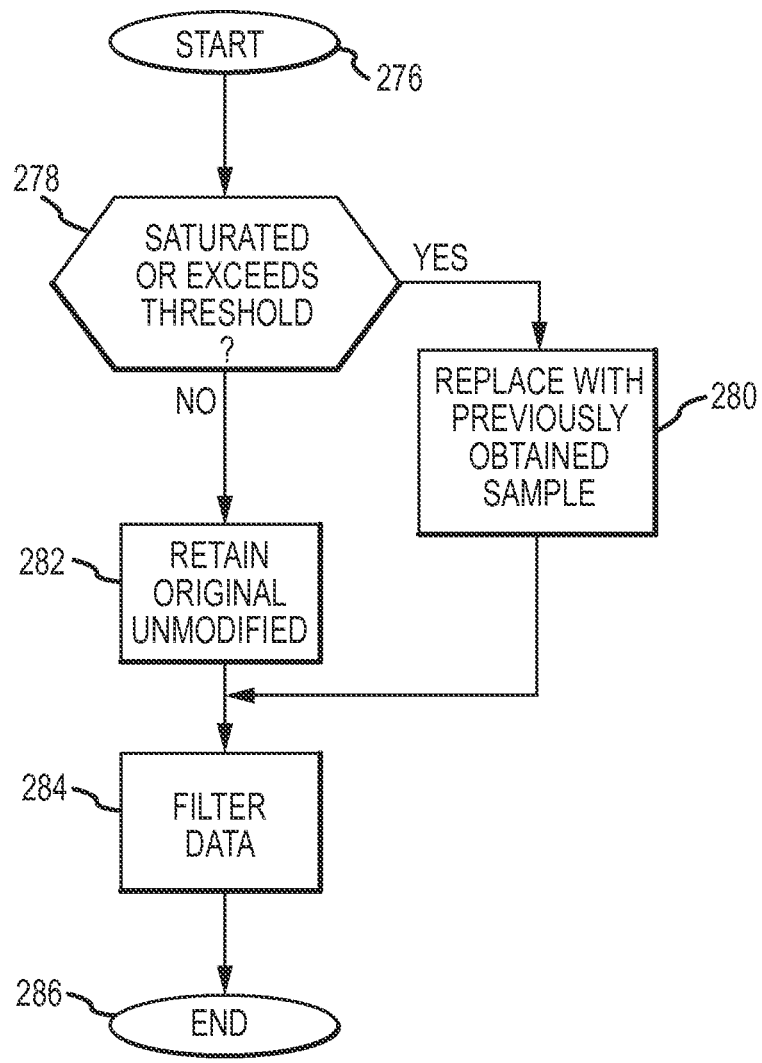
FIG. 11 is a flowchart showing another embodiment of the noise mitigation logic of FIG. 9.

FIG. 11 is a flowchart showing the processing that occurs through the execution of mitigation logic 246b, in an alternate embodiment. The method of FIG. 11 consolidates the logic used into one test, with the observation that an input that exceeds a threshold may include the saturation case. The method begins in step 276, and proceeds to step 278.

In step 278, the mitigation logic 246b includes a mechanism to determine whether the ADC 232 input has been saturated, indicating that a significant noise pulse occurred and has corrupted the measurement, or has exceeded a predetermined threshold indicating the presence of noise. If the answer is "YES", then the method branches to step 280.

In step 280, the mitigation logic 246b replaces the digital signal 262 with a digital sample taken or measured during the immediately preceding cycle or pattern of excitation activity (i.e., the sample acquired 10 time-slices previous, in the described embodiment). The mitigation logic 246b is then configured to insert the replacement sample into the data stream, which is then handled (demodulated) in accordance with normal processing. However, if the answer in step 278 is "NO", then the method proceeds to step 282 (retain original sample unmodified). The method then proceeds to step 284.

In step 284, the digital signal is filtered. In this step, the logic 246b removes noise from the digital signal. For example, the mitigation logic 246b, in an embodiment, includes digital filters which are configured to be reasonably effective and which reduce the level of interference to acceptable levels. The method ends in step 286.

Thus, the method of FIG. 11 involves substituting (replacing) an impedance measurement with one previously-obtained in response to exceeding a threshold, as opposed to just filtering as was done in the method of FIG. 10 when the data is below the saturation level.

The mitigation logic can also be configured to substitute (replace) of an impedance measurement with one previously-obtained when saturation and/or exceeding a threshold occurs at other nodes in the system (not just at the ADC input). The mitigation logic can then be configured to perform such substitution upon occurrence of at least one pre-condition selected from the group comprising a local saturation condition at a node in the system other than the ADC input and exceeding a local threshold condition at a node in the system other than the ADC input.

It should be understood that variations are possible. For example, the current Ensite™ NavX™ Velocity™ platform (as implemented) requires a full ten-time-slice period of interference-free signal, which places restrictions on the MR pulse sequences and reduces the efficiency of MR imaging (when used in an MRI environment). Accordingly, in a Velocity™-based EAM system 196 embodiment, the Velocity™ implementation can be modified to require only a single time-slice of interference-free signal.

In addition, noise-mitigation embodiments (i.e., systems 196) may have, but do not require, compatibility with high fidelity ECG or egram signals.

An advantage of replacing an impedance sample that is subject to corruption with a previously-obtained sample is that it allows the rest of the system to operate without modification. By replacing the samples that are subject to corruption with samples that are not subject to corruption, the down-stream software which uses these impedance samples can remain uninformed of the potential for noise contamination and ultimate mitigation through replacement—thereby simplifying the system design and allowing the already-available system software to operate in this noisy environment.

It should also be appreciated that such embodiments may be used to provide MRI-compatible) electrode tracking as well as catheter-based EA mapping and/or point collection for geometry generation, for both cardiac applications as well as non-cardiac applications (e.g., renal/kidney vessels and related nerves, brain, spine, prostate, stomach, lung, peripheral blood vessels including carotids, aorta, including abdominal aortic aneurism (AAA), and the like). It should likewise be appreciated that such MRI-compatibility extends to MRI systems of diverse field strength, for example, 1.5T, 3T, 7T, etc.

It should also be understood that noise-mitigation embodiments (i.e., systems 196) may, but need not, be used in combination with other approaches address issues that arise in the MRI environment, such as metallic heating issues and MR image distortion artifacts due to metallic conductors/members in the MR field, for example only as seen by reference to US Pat. Pub. 2008/0262584 filed 13 Mar. 2008 (Ser. No. 12/047,832, the '832 application); and US Pat. Pub. 2008/0269591 filed 30 Oct. 2008 (Ser. No. 12/170,811, the '811 application). The '832 application and the '811 application are both hereby incorporated by reference in their entireties.

It should be further understood that signals emanating from diverse sensors may also be handled through the noise-mitigation schemes (systems 196) described herein, such as those pertaining to blood oximetry ($SaO_2$, $SvO_2$, and $PD_x$), 1-, 2-, 3-dimensional accelerometers for patient motion/respiration artifact compensation, blood pressure and the like.

It should be further understood that noise-mitigation embodiments (i.e., systems 196) may, but need not, be used in connection various optical sensor schemes, which have inherent MRI-compatibility.

It should be further understood that noise-mitigation embodiments (i.e., systems 196) may, but need not, be employed in an overall navigation system where: (1) MR imaging can be co-registered with Ensite™ (Electro Anatomical) mapping geometries; (2) MR imaging and EAM-images are registered to sensor output signals; (3) EGM/ECG traces are registered to various imaging such as operating room fluoroscopic imaging/static X-ray imaging; and (4) any combination of the foregoing.

It should be further understood that noise-mitigation embodiments (i.e., systems 196) can be used with diverse MRI procedures, such as adding MRI contrast media including post-procedure for Delayed Enhancement (DE) lesion visualization in vivo via MRI.

It should be appreciated that noise-mitigation embodiments (i.e., systems 196) enable enhanced functionality in connection with an MRI session. For example, such noise-mitigation systems 196 may be embodied in relatively mobile computing assets, such as a laptop computer or other mobile computer (e.g., desktop on wheeled-cart), such that a properly secured patient can be moved into and out of an MRI bore with uninterrupted (continuous) catheter tracking, wherein such patient can then further be moved into or to an interventional operating room (OR) suite (e.g., including fluoroscopy or other imaging modalities), and then further to a traditional catheter lab, to an EP-implanting suite for IPG (e.g., heart, spine, etc.) or ICD and the like implant.

It should be further understood that noise-mitigation embodiments (i.e., systems 196) can be used in connection with tracking ablation catheters for use in ablation procedures. Ablation energy sources may include radio frequency (RF) energy, high-intensity focused ultrasound (HIFU) energy, cryogenic, microwave, chemical and the like.

It should be further understood that during blanking (or periods where acquired signals are discarded or ignored) by virtue of MR-related noise inducing conditions, that such time periods can be used to conduct ablation in accordance with any of the modalities described above. As a further features, such ablation procedure may take into account the incremental energy provided by the MR imaging system (i.e., energy delivered to target tissue by virtue of MR Imaging can be taken into account in prescribing how much energy to deliver via an RF ablation electrode or other ablation instrumentality).

In an embodiment, an article of manufacture is provided for mitigating the effects of potentially corrupted positioning signals (i.e., impedance measurements) due to external noise inducing conditions, such as those present during an MRI scan. In accordance with another embodiment, the article of manufacture includes a computer storage medium having a computer program encoded thereon, where the computer program includes code for determining a device electrode position based on a plurality of impedance measurements taken with respect to the electrode, and identifying one or more of the impedance measurements taken during an external noise inducing condition and which are subject to corruption. The computer program includes further code for replacing the one or more identified impedance measurements in accordance with a predetermined mitigation strategy. Such embodiments may be configured to execute one or more processors, multiple processors that are integrated into a single system or are distributed over and connected together through a communications network, and where the network may be wired or wireless.

A magnetic resonance imaging (MRI) system comprises a magnet system configured to generate a polarizing magnetic field about at least a portion of a patient arranged in the MRI system, a plurality of gradient coils configured to apply a gradient field to the polarizing magnetic field, a radio frequency (RF) system configured to apply an excitation field to the patient and acquire MR image data therefrom, a localization system arranged to obtain impedance measurements with respect to at least one electrode of an invasive medical device, the localization system being further configured to determine a position of said device electrode; and mitigation logic configured to identify one or more of said impedance measurements taken during an external noise inducing condition and which are subject to corruption, the mitigation logic being further configured to replace the one or more identified impedance measurements in accordance with a predetermined mitigation strategy.

An apparatus for generating a three-dimensional (3D) geometry of at least a portion of an internal organ and tracking a medical device within the at least a portion of the internal organ within an externally-applied three-axis field imposed across the internal organ via a processor-based apparatus, comprises: at least one tracking element coupled to a medical device, wherein the tracking device is adapted to respond to an external three-axis electromagnetic field imposed over a minor volume of organ tissue of a subject, wherein the subject is secured to a base member; an organ geometry generating apparatus for producing the three-axis field and for coupling same to the at least one tracking element, wherein the organ geometry generating apparatus includes one of a signal blanking and a switching capability based at least in part upon an magnetic field imposed over a major volume of organ tissue via an external MRI scanner; and means for moving the processor-based apparatus in concert with any gross movement of the base member and the subject while not disrupting the external three-axis field or the coupling between the organ geometry generating apparatus and the medical device.

The above-described apparatus for generating a three-dimensional (3D) geometry, wherein the tracking element comprises one of a current-carrying electrode, an electrode exposed to a positive or negative voltage, and a metallic coil.

The above-described apparatus for generating a three-dimensional (3D) geometry, wherein the organ geometry generating apparatus comprises an impedance-based electro-anatomic mapping (EAM) system, and wherein the EAM system comprises a magnetic-based EAM system.

The above-described apparatus for generating a three-dimensional (3D) geometry, further comprising at least one physiologic sensor coupled to the subject and having a sensor output signal coupled to the organ geometry generating apparatus, and wherein the at least one physiologic sensor comprises one of: a saturated arterial oxygen sensor, a saturated venous oxygen sensor, a partial blood oxygen sensor, a blood pressure sensor, and an accelerometer, wherein the accelerometer comprises one of a two-axis accelerometer and a three-axis accelerometer and the output signal therefrom couples to a subject motion correction circuit.

The above-described apparatus for generating a three-dimensional (3D) geometry (or any combination of features thereof), further comprising a graphical user interface for displaying at least one of the 3D geometry and a location of the at least one tracking element relative to the minor volume of organ tissue.

The above-described apparatus for generating a three-dimensional (3D) geometry, wherein the base member is movable and configured to accommodate at least the processor-based apparatus such that the subject and the processor-based apparatus move substantially in concert.

The above-described apparatus for generating a three-dimensional (3D) geometry, wherein the moving means comprises one of wheels, tracks, rails or a combination of one or more of the foregoing.

It should be understood that an electronic controller or ECU as described above for certain embodiments may include conventional processing apparatus known in the art, capable of executing pre-programmed instructions stored in an associated memory, all performing in accordance with the functionality described herein. To the extent that the methods described herein are embodied in software, the resulting software may be stored in an associated memory and where so described, may also constitute the means for performing such methods. Implementation of certain embodiments of the invention, where done so in software, would require no more than routine application of programming skills by one of ordinary skill in the art, in view of the foregoing enabling description. An electronic controller or ECU may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the invention as defined in the appended claims.

The invention claimed is:

1. A noise-tolerant apparatus for determining a position of an electrode of an invasive medical device, comprising:
an electronic control unit (ECU) and a computer-readable memory coupled to said ECU;
an electro-anatomical mapping system configured to selectively drive, during a respective time slice, an excitation signal across a respective one of a plurality of paired body surface electrodes and to repeat excitation through a pattern of paired surface electrodes;
said mapping system being further configured to acquire, during said time slices, a respective resultant signal from said device electrode;
said mapping system being further configured to determine, for each time slice, a respective impedance measurement based on at least said resultant signal wherein at a boundary of each time slice said impedance measurements are discontinuous as being taken from different body surface electrode pairs;
position determining logic stored in said memory configured to be executed by said ECU, said position determining logic being configured to determine said device electrode position based on a plurality of impedance measurements taken with respect to said electrode; and
mitigation logic stored in said memory configured to be executed by said ECU, said mitigation logic being configured to identify one or more of said impedance measurements taken during an external noise inducing condition and which are subject to corruption, said mitigation logic being further configured to replace said one or more identified impedance measurements in accordance with a predetermined mitigation strategy, said predetermined mitigation strategy includes substituting a previously-obtained impedance measurement for said identified impedance measurement, said previously-obtained impedance measurement being associated with the same body surface electrode pair as was used to obtain said identified impedance measurement subject to corruption.

2. The apparatus of claim 1 wherein said predetermined mitigation strategy includes substituting, in response to a synchronization signal, said previously-obtained impedance measurement for said identified impedance measurement, said synchronization signal being indicative of said external noise inducing condition.

3. The apparatus of claim 2 wherein said apparatus includes an input port for receiving said synchronization signal, said mitigation logic being configured to respond to a synchronization parameter whose logic state corresponds to the state of the synchronization signal.

4. The apparatus of claim 3 wherein said mitigation logic is configured to monitor the synchronization parameter and determine a time when the state of the synchronization parameter is asserted to indicate that said external noise inducing condition exists, said mitigation logic being further configured to use said determined time to identify the one or more time slices where said corresponding one or more impedance measurements may be corrupted by noise.

5. The apparatus of claim 3 wherein said mitigation logic is configured to store impedance measurements for said plurality of paired body surface electrodes in a buffer;
wherein said determined time when said synchronization parameter is asserted is anticipatory with respect to a time slice in which noise and signal corruption is expected, wherein said mitigation logic retrieves an impedance measurement from said buffer corresponding to the time slice in which the noise is anticipated and inserts said retrieved impedance measurement in the sequence of impedance measurements.

6. The apparatus of claim 3 wherein said mitigation logic is configured to store impedance measurements for said plurality of paired body surface electrodes in a buffer;
wherein said determined time when said synchronization parameter is asserted is after the beginning of a time slice in which noise and signal corruption is expected, wherein said mitigation logic delays output of said corrupted impedance measurement, retrieves an impedance measurement from said buffer corresponding to the time slice in which the noise and signal corruption is expected, and inserts said retrieved impedance measurement in the sequence of impedance measurements.

7. The apparatus of claim 2 wherein said mitigation logic is configured to determine when said resultant signal saturates an analog-to-digital converter (ADC) input and in response thereto perform said substituting of said previously-obtained measurement.

8. The apparatus of claim 2 wherein said mitigation logic is configured to determine when said resultant signal exceeds a predetermined threshold but does not saturate an analog-to-digital converter (ADC) input and in response thereto filtering said resultant signal.

9. The apparatus of claim 2 wherein said mitigation logic is configured to determine when said resultant signal exceeds a predetermined threshold and in response thereto perform said substituting of said previously-obtained measurement.

10. The apparatus of claim 2 wherein said mitigation logic is configured to perform said substituting of said previously-obtained measurement upon occurrence of at least one pre-condition selected from the group comprising a local saturation condition in said apparatus and exceeding a local threshold condition in said apparatus.

11. The apparatus of claim 1 wherein said external noise inducing condition is selected from the group comprising magnetic gradients ramps in an magnetic resonance imaging (MRI) environment, radio-frequency (RF) pulses in said MRI environment, and electromagnetic field generation in a magnetic-field based localization system environment.

12. A noise-tolerant apparatus for determining a position of an electrode of an invasive medical device, comprising:
an electronic control unit (ECU) and a computer-readable memory coupled to said ECU;

means for selectively driving, during a respective time slice, an excitation signal across a respective one of a plurality of paired body surface electrodes, said driving means being controlled to repeat excitation through a pattern of paired surface electrodes;

means for acquiring, during said time slices, a respective resultant signal from said device electrode;

means for determining, for each time slice, a respective impedance measurement based on at least said resultant signal, wherein at a boundary of each time slice said impedance measurements are discontinuous as being taken from different body surface electrode pairs;

position determining logic stored in said memory configured to be executed by said ECU, said position determining logic being configured to determine said device electrode position based on a plurality of impedance measurements taken with respect to said electrode; and mitigation logic stored in said memory configured to be executed by said ECU, said mitigation logic being configured to identify one or more of said impedance measurements taken during an external noise inducing condition and which are subject to corruption, said mitigation logic being further configured to substitute one or more previously-obtained impedance measurements for said identified one or more impedance measurements in accordance with a predetermined mitigation strategy, wherein said one or more previously-obtained impedance measurements are respectively associated with the same body surface electrode pair as was used to obtain said one or more identified impedance measurements subject to corruption.

13. The apparatus of claim 12 wherein a synchronization signal is indicative of said external noise inducing condition.

14. The apparatus of claim 13 wherein said apparatus includes an input port for receiving said synchronization signal, said mitigation logic being configured to respond to a synchronization parameter whose logic state corresponds to the state of the synchronization signal.

15. The apparatus of claim 14 wherein said mitigation logic is configured to monitor the synchronization parameter and determine a time when the state of the synchronization parameter is asserted to indicate that said external noise inducing condition exists, said mitigation logic being further configured to use said determined time to identify the one or more time slices where said corresponding one or more impedance measurements may be corrupted by noise.

16. The apparatus of claim 14 wherein said mitigation logic is configured to store impedance measurements for said plurality of paired body surface electrodes in a buffer, said mitigation logic being configured to:

(i) retrieve an impedance measurement from said buffer corresponding to the time slice in which the noise is anticipated and insert said retrieved impedance measurement in the sequence of impedance measurements when said determined time when said synchronization parameter is asserted is anticipatory with respect to a time slice in which noise and signal corruption is expected; and (ii) delay output of said corrupted impedance measurement, retrieve an impedance measurement from said buffer corresponding to the time slice in which the noise and signal corruption is expected, and insert said retrieved impedance measurement in the sequence of impedance measurements, when said determined time when said synchronization parameter is asserted is after the beginning of a time slice in which noise and signal corruption is expected.

17. The apparatus of claim 13 wherein said apparatus includes a mechanism to produce a saturation signal when said resultant signal saturates an analog-to-digital converter (ADC) input, said saturation signal corresponding to said synchronization signal.

18. The apparatus of claim 17 wherein said mitigation strategy includes filtering said impedance measurement when said resultant signal exceeds a predetermined threshold but does not saturate said ADC input.

19. An article of manufacture, comprising:

a non-transitory computer storage medium having a computer program including instructions encoded thereon for determining a device electrode position of an invasive medical device based on a plurality of impedance measurements taken during a respective time slice with respect to said electrode wherein said plurality of impedance measurements correspond to a respective one of a plurality of paired body surface electrodes wherein at a boundary of each time slice said impedance measurements are discontinuous as being taken from different body surface electrode pairs, for identifying one or more of said impedance measurements taken during an external noise inducing condition and which are subject to corruption, and for replacing the one or more identified impedance measurements in accordance with a predetermined mitigation strategy, wherein said predetermined mitigation strategy includes substituting a previously-obtained impedance measurement for said identified impedance measurement, said previously-obtained impedance measurement being associated with the same body surface electrode pair as was used to obtain said identified impedance measurement subject to corruption.

20. The article of manufacture of claim 19 wherein said source of noise inducing conditions is a magnetic resonance imaging (MRI) system, and wherein the program further responds to a synchronization signal indicative of when said conditions are present.

* * * * *